US008876376B2

(12) United States Patent
Archibald

(10) Patent No.: US 8,876,376 B2
(45) Date of Patent: Nov. 4, 2014

(54) ALIGNMENT DEVICE FOR BITEWING RADIOGRAPH

(76) Inventor: Valerie Archibald, Ottawa (CA)

( * ) Notice: Subject to any disclaimer, the term of this patent is extended or adjusted under 35 U.S.C. 154(b) by 282 days.

(21) Appl. No.: 13/377,469

(22) PCT Filed: Jun. 8, 2010

(86) PCT No.: PCT/CA2010/000850
§ 371 (c)(1),
(2), (4) Date: Dec. 9, 2011

(87) PCT Pub. No.: WO2010/142020
PCT Pub. Date: Dec. 16, 2010

(65) Prior Publication Data
US 2012/0076268 A1      Mar. 29, 2012

Related U.S. Application Data

(60) Provisional application No. 61/185,634, filed on Jun. 10, 2009.

(51) Int. Cl.
*A61B 6/14*     (2006.01)
*A61B 6/04*     (2006.01)

(52) U.S. Cl.
CPC . *A61B 6/14* (2013.01); *A61B 6/145* (2013.01); *A61B 6/0492* (2013.01); *A61B 6/04* (2013.01)
USPC ............................................. 378/170

(58) Field of Classification Search
USPC .......................................... 378/170
See application file for complete search history.

(56) References Cited

U.S. PATENT DOCUMENTS

| | | |
|---|---|---|
| 5,609,170 A | 3/1997 | Roth |
| 6,102,566 A | 8/2000 | Willis |
| 2002/0100134 A1* | 8/2002 | Dunn et al. ............ 15/167.1 |
| 2007/0041506 A1 | 2/2007 | Bottino |
| 2008/0019579 A1 | 1/2008 | Crucs |
| 2008/0025467 A1 | 1/2008 | Diederich |
| 2009/0168969 A1 | 7/2009 | Schmulenson et al. |

OTHER PUBLICATIONS

Supplemental EP Search report for 10785618.9 dated May 29, 2013.

* cited by examiner

*Primary Examiner* — Glen Kao
(74) *Attorney, Agent, or Firm* — O'Shea Getz P.C.

(57) ABSTRACT

An alignment device for a bitewing radiograph includes a longitudinally extending handle having a first end and a second end and a tip disposed at the second end and extending orthogonally to the handle, wherein a length of the tip is substantially less than a length of the handle and wherein a cross-sectional area of the tip is substantially less than a cross-sectional area of the handle. This alignment device enables a dentist or other x-ray operator to easily and quickly align a bitewing radiograph so as to obtain a diagnostic non-overlapping x-ray of crooked teeth in a patient's mouth. The alignment device may optionally include a slidable rubber ring or a slidable hub with rod. The ring and hub are dimensioned to slide over the handle to facilitate the lining up of the x-ray cone.

18 Claims, 2 Drawing Sheets

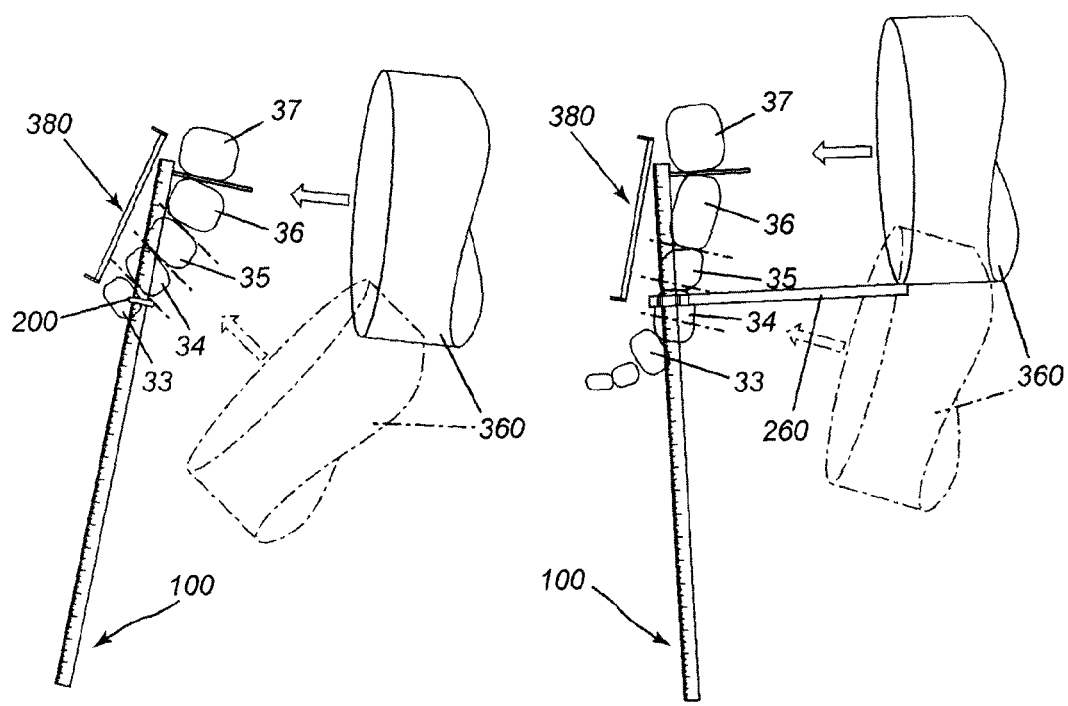
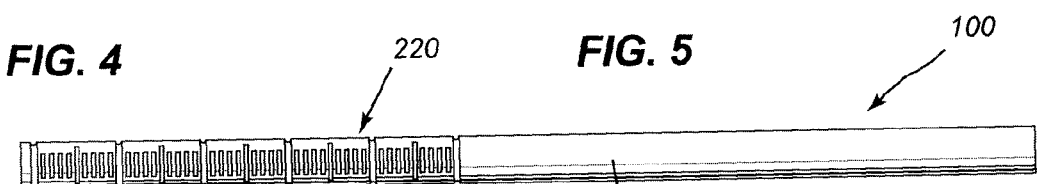
FIG. 4  FIG. 5
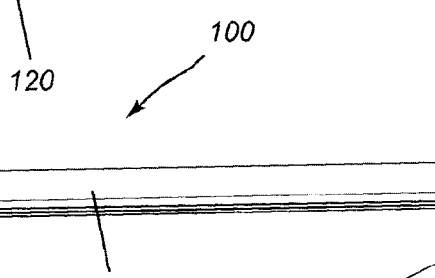
FIG. 6
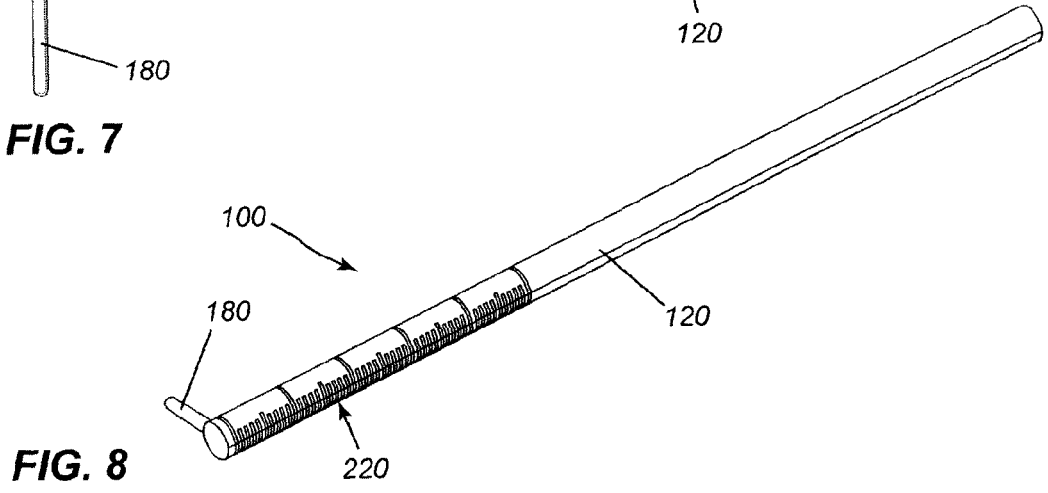
FIG. 7
FIG. 8

ALIGNMENT DEVICE FOR BITEWING RADIOGRAPH

This patent application claims priority from PCT Patent Application No. PCT/CA2010/000850 filed Jun. 8, 2010, which claims priority to U.S. Provisional Application No. 61/185,634 filed Jun. 10, 2009, both of which are hereby incorporated by reference in their entireties.

TECHNICAL FIELD

The present invention relates generally to dentistry and, in particular, to techniques for taking oral radiographs.

BACKGROUND

Current x-ray technologies work well for patients with straight teeth and nicely curving arches. However, many patients have teeth that are crooked. The result is x-rays that are non-diagnostic and cannot be used. Dentists and x-ray operators must repeatedly guess the angle of the mal-alignment and match that to the x-ray cone.

While the well-known Rinn holder (see, e.g. http://www.rinncorp.com/) is useful for preventing cone cuts, this device does not address the specific problem of aligning the x-ray cone and radiographic film for patients having crooked teeth or patients with unusually curved arches.

As a result of this problem, productive billing time for the dentist or x-ray operator is lost. It is estimated that each x-ray takes approximately two minutes to take and seven minutes to develop and analyze. Dentists may typically only bill for the clear x-ray images. Having to re-take the bitewing x-rays means not only lost billing time but also added cost of wasted x-ray films. For the patient, this represents inconvenience and a delay in diagnosis and treatment, not to mention extra exposure to x-ray radiation. Overall, the inability to reliably position a bitewing for x-raying crooked teeth is frustrating for dentists, x-ray operators and patients alike. There is thus a need in dentistry for a device and method that addresses this technical problem.

SUMMARY

In broad terms, the present invention is an alignment device for bitewing radiographs. This alignment device is a tool that a dentist, hygienist, dental assistant or other x-ray operator can easily use to determine the proper angle or orientation of an x-ray cone for the taking of a bitewing radiograph. This novel alignment device thus enables a new method of taking bitewing radiographs in which this alignment device is placed between crooked teeth to determine a proper angle for subsequently taking a bitewing radiograph.

Accordingly, one main aspect of the present invention is an alignment device for a bitewing radiograph. The device comprises a longitudinally extending handle having a first end and a second end and a tip disposed at the second end and extending orthogonally to the handle, wherein a length of the tip is substantially less than a length of the handle and wherein a cross-sectional area of the tip is substantially less than a cross-sectional area of the handle.

In particular embodiments of this invention, the alignment device may further include a marking ring, for example made of rubber or equivalent, that can be slid along the handle for marking the radius of the x-ray cone being used.

In other embodiments of the invention, the alignment device has a movable hub that is dimensioned to be manually displaced along the length of the handle. A rod is affixed to the movable hub and extends orthogonally from the handle and parallel to the tip.

A further main aspect of the present invention is a method of taking a bitewing radiograph. This method entails inserting into a mouth of a patient an alignment device comprising a longitudinally extending handle having a first end and a second end and a tip disposed at the second end and extending orthogonally to the handle, wherein a length of the tip is substantially less than a length of the handle and wherein a cross-sectional area of the tip is substantially less than a cross-sectional area of the handle. The method further entails aligning the tip between two adjacent teeth, the handle thereby providing visual guidance for positioning an x-ray cone for taking the bitewing radiograph.

Yet a further main aspect of the present invention is a method of taking a bitewing radiograph. This method comprises inserting into a mouth of a patient an alignment device comprising a longitudinally extending handle having a first end and a second end and a tip disposed at the second end and extending orthogonally to the handle, aligning the tip between two adjacent teeth, the handle thereby protruding outwardly from the mouth of the patient, positioning an x-ray cone, instructing the patient to hold still, removing the device, inserting the film, taking the bitewing radiograph using the x-ray cone, and developing the bitewing radiograph.

Other aspects, features and advantages of this novel technology will become apparent with reference to the following description and drawings.

BRIEF DESCRIPTION OF THE DRAWINGS

Further features and advantages of the present invention will become apparent from the following detailed description, taken in combination with the appended drawings, in which:

FIG. 4 depicts how the alignment device presented in FIG. 1 is used to align an x-ray cone for taking a bitewing radiograph;

FIG. 5 depicts how the alignment device presented in FIG. 2 is used to align an x-ray cone for taking a bitewing radiograph; and FIG. 6 is a top plan view of an alignment device in accordance with another embodiment of the present invention;

FIG. 7 is a side elevation view of the alignment device of FIG. 6; and

FIG. 8 is an isometric view of the alignment device of FIG. 6.

It will be noted that throughout the appended drawings, like features are identified by like reference numerals. It should furthermore be noted that the drawings are not necessarily to scale.

DETAILED DESCRIPTION

In general, and by way of overview, the present invention provides an alignment device that facilitates the task of taking a bitewing radiograph of crooked teeth. In operation, a tip of the alignment device is placed between two adjacent teeth in the patient's mouth. The handle orthogonal to the tip thus provides visual guidance to facilitate orientation and alignment of the x-ray cone being used to take the bitewing radiograph.

Main illustrative embodiments of this invention are now described below having regard to the appended figures.

Figure 1:
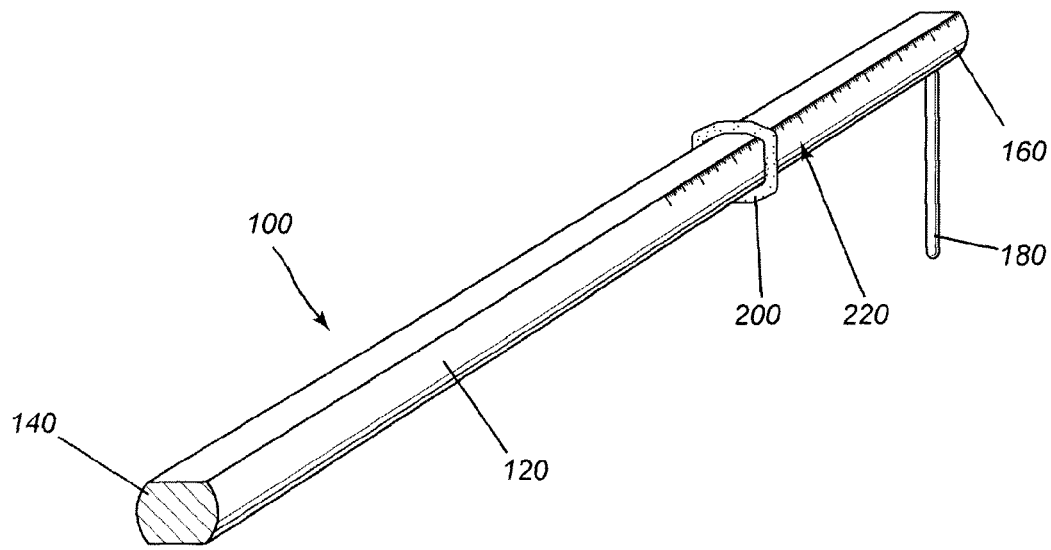
FIG. 1 is an isometric view of an alignment device for taking a bitewing radiograph in accordance with one embodiment of the present invention.
Figure 2:
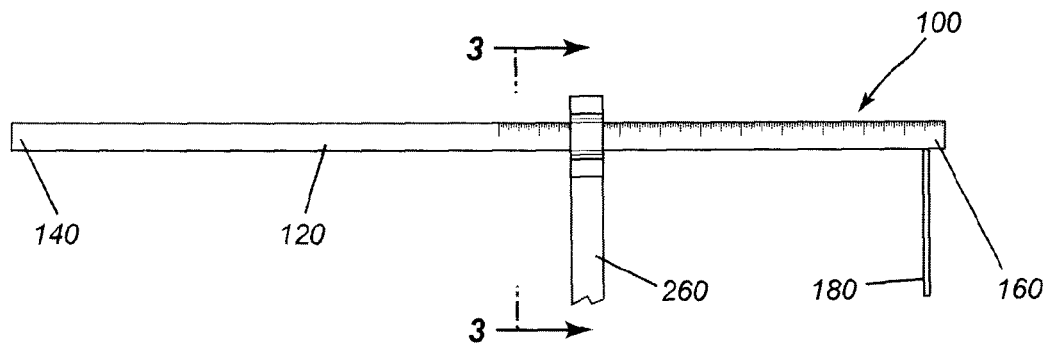
FIG. 2 is a side elevation view of an alignment device having a hub and rod in accordance with another embodiment of the present invention.

FIG. 1 is an isometric view of an alignment device for taking a bitewing radiograph in accordance with one embodiment of the present invention. The alignment device, which is generally designated by reference numeral 100 in this figure, comprises a longitudinally extending handle 120 having a first end 140 and a second end 160. As can be seen from the embodiment shown in FIG. 1 (and also in the embodiments shown in FIGS. 2 and 6-8), the handle may have a uniform cross-sectional area along the longitudinally extent of the handle 120. The device 100 also includes a tip 180 disposed at the second end and extending orthogonally to the handle. As illustrated, a length of the tip (or "probe") is substantially less than a length of the handle. A cross-sectional area of the tip is substantially less than a cross-sectional area of the handle.

The alignment device may optionally include a marking ring 200 that is dimensioned to be manually displaced along the length of the handle for marking the radius of an x-ray cone being used to take the bitewing radiograph. The marking ring in one embodiment may be a coloured rubber ring. Optionally, the handle may have length markings 220 (like on a ruler) extending from the second end toward the first end. The ring thus facilitates lining up of the x-ray cone.

The handle of the alignment device may optionally be made of a soft plastic for patient comfort. The handle may also have a ribbed or bumpy outer surface, making the handle more comfortable for the patient to bite.

A disposable variant of the alignment device may also be provided. Whereas the version shown in FIG. 1 is meant to be reusable, a disposable version may be discarded after usage. Whereas the embodiment shown in FIG. 1 may have a metal tip, the disposable version would preferably have a plastic tip.

Figure 3:
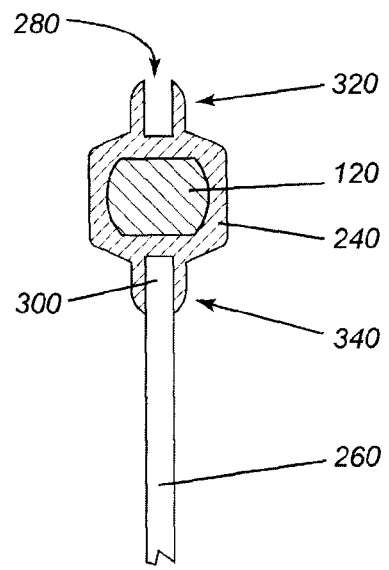
FIG. 3 is an enlarged front view of the hub and rod shown in FIG. 2.

FIG. 3 is a front view of an alignment device having a slidable hub 240 and a 260 rod in accordance with another embodiment of the present invention. In other words, the alignment device in accordance with this variant has a movable hub 240 that is dimensioned to be manually displaced along the length of the handle and a rod 260 affixed to the movable hub and extending orthogonally from the handle and parallel to the tip. Preferably, a length of the rod is greater than a length of the tip.

As shown in the embodiment depicted in FIG. 3, the hub comprises first and second sockets 280, 300 disposed on opposing sides 320, 340 of the hub 240, each of the first and second sockets 280, 300 being dimensioned to securely hold the rod 260.

FIG. 4 depicts an occlusal view of mal-aligned teeth and how the alignment device 100 presented in FIGS. 1a-2b is used to align an x-ray cone 360 for taking a bitewing radiograph 380. FIG. 4 shows teeth 33, 34, 35, 36, 37 (labelled according to international tooth codes). The alignment device may be used as follows: (1) measure the diameter of the x-ray cone and divide by two to obtain the radius of the x-ray cone. Set the rubber ring to mark the radius. As will be appreciated in light of the foregoing discussion, use of the rubber ring is optional; (2) instruct the patient to hold still; (3) line up the tip ("probe end") on the contact in the direction needed for the x-ray beam to pass through; (4) line up the x-ray cone perpendicular to the handle; (5) bring the edge of the cone in line with the rubber ring to prevent cone cut (as mentioned above, use of the rubber ring is optional); (6) instruct the patient to slowly open without moving his or her head; (7) insert the film with a tab or holder, but not with a Rinn; and (8) take the bitewing radiograph and expose film. As shown in FIG. 4, the alignment device helps the user (dentist, dental assistant, etc.) to find the correct angle to open up the 36/37 contact. Once the correct angle is found, the bitewing is inserted and the radiograph taken to provide a clear and unobstructed (non-overlapping) image of teeth 36 and 37.

FIG. 5 depicts an occlusal view of mal-aligned teeth and how the alignment device 100 presented in FIGS. 3a-3b (having hub 240 and rod 260) is used to align an x-ray cone 360 for taking a bitewing radiograph 380. As was the case with FIG. 4, FIG. 5 also shows teeth 33, 34, 35, 36, 37 (labelled according to international tooth codes). The procedure for using this version of the alignment device is similar to what was described above except that the rod and hub is employed in lieu of the rubber ring.

FIGS. 6 to 8 depict a further embodiment of the present invention. In this further embodiment, the handle 120 of the alignment device 100 has a circular cross-section. A ring (or hub and rod) with a circular inside profile may optionally be added to this embodiment of the alignment device. However, it should be noted that this alignment device has been found to function perfectly well without a ring (or hub and rod).

This novel alignment device greatly facilitates the taking of diagnostic bitewing radiographs. The alignment device helps to ensure that the bitewing radiograph is perpendicular to the x-ray cone, thus greatly improving the prospects of obtaining a clear image that enables the dentist to identify or rule out decay. This new technology saves both time and cost to the dentist, and enables a more rapid diagnosis of mal-aligned teeth by eliminating the guesswork in taking bitewing radiographs of mal-aligned teeth.

In addition, this novel alignment device may be used for taking a periapical film.

The present invention has been described in terms of specific embodiments, examples, implementations and configurations which are intended to be exemplary or illustrative only. Other variants, modifications, refinements and applications of this innovative technology will become readily apparent to those of ordinary skill in the art who have had the benefit of reading this disclosure. Such variants, modifications, refinements and applications fall within the ambit and scope of the present invention. Accordingly, the scope of the exclusive right sought by the Applicant for the present invention is intended to be limited solely by the appended claims and their legal equivalents.

The invention claimed is:

1. An alignment device for a bitewing radiograph, the device comprising:
    a longitudinally extending handle having a first end and a second end; and
    a tip disposed at the second end and extending orthogonally to the handle, wherein a length of the tip is substantially less than a length of the handle and wherein a cross-sectional area of the tip is substantially less than a cross-sectional area of the handle; and
    a marking ring that is dimensioned to be manually displaced along the length of the handle for marking the radius of an x-ray cone being used to take the bitewing radiograph.

2. The alignment device as claimed in claim 1, wherein the cross-sectional area of the tip is uniform.

3. The alignment device as claimed in claim 2 wherein the marking ring is a coloured rubber ring.

4. The alignment device as claimed in claim 1 wherein the handle is made of a soft plastic for patient comfort.

5. The alignment device as claimed in claim 1 wherein the handle is made of a soft plastic with a ribbed outer surface.

6. The alignment device as claimed in claim 1 further comprising:
   a movable hub that is dimensioned to be manually displaced along the length of the handle; and
   a rod affixed to the movable hub and extending orthogonally from the handle and parallel to the tip.

7. The alignment device as claimed in claim 6 wherein the hub comprises first and second sockets disposed on opposing sides of the hub, each of the first and second sockets being dimensioned to securely hold the rod.

8. The alignment device as claimed in claim 6 wherein a length of the rod is greater than a length of the tip.

9. The alignment device as claimed in claim 1 wherein the handle comprises length markings extending from the second end toward the first end.

10. The alignment device as claimed in claim 1 wherein the cross-sectional area of the handle is uniform.

11. A method of aligning a bitewing radiograph, the method comprising:
    inserting into a mouth of a patient an alignment device comprising a longitudinally extending handle having a first end and a second end and a tip disposed at the second end and extending orthogonally to the handle, wherein a length of the tip is substantially less than a length of the handle and wherein a cross-sectional area of the tip is substantially less than a cross-sectional area of the handle;
    aligning the tip between two adjacent teeth, the handle thereby providing visual guidance for positioning an x-ray cone for taking the bitewing radiograph; and
    positioning the x-ray cone using the alignment device.

12. The method as claimed in claim 11 further comprising sliding a ring over the handle for lining up the x-ray cone.

13. The method as claimed in claim 11 further comprising sliding a hub over the handle, the hub supporting a rod extending orthogonally to the handle for lining up the x-ray cone.

14. The method as claimed in claim 13 further comprising a preceding step of inserting the rod into a socket in the hub.

15. A method of taking a bitewing radiograph, the method comprising:
    inserting into a mouth of a patient an alignment device comprising a longitudinally extending handle having a first end and a second end and a tip disposed at the second end and extending orthogonally to the handle;
    aligning the tip between two adjacent teeth, the handle thereby protruding outwardly from the mouth of the patient;
    positioning an x-ray cone;
    instructing the patient to hold still;
    removing the device from the mouth of the patient;
    instructing the patient to open;
    inserting the bitewing radiograph;
    instructing the patient to close;
    taking the bitewing radiograph using the x-ray cone; and
    developing the bitewing radiograph.

16. The method as claimed in claim 15 further comprising sliding a ring over the handle for lining up an x-ray cone.

17. The method as claimed in claim 15 further comprising sliding a hub over the handle, the hub supporting a rod extending orthogonally to the handle for lining up an x-ray cone.

18. The method as claimed in claim 17 further comprising a preceding step of inserting the rod into a socket in the hub.

\* \* \* \* \*